United States Patent
Fain et al.

(10) Patent No.: US 10,585,074 B2
(45) Date of Patent: Mar. 10, 2020

(54) METHOD OF FABRICATING A MEMS AND/OR NEMS STRUCTURE COMPRISING AT LEAST TWO ELEMENTS SUSPENDED FROM A SUPPORT AT DIFFERENT DISTANCES FROM SAID SUPPORT

(71) Applicant: COMMISSARIAT A L'ENERGIE ATOMIQUE ET AUX ENERGIES ALTERNATIVES, Paris (FR)

(72) Inventors: Bruno Fain, Grenoble (FR); Carine Ladner, Voiron (FR); Thomas Alava, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 72 days.

(21) Appl. No.: 15/873,136

(22) Filed: Jan. 17, 2018

(65) Prior Publication Data
US 2018/0202982 A1 Jul. 19, 2018

(30) Foreign Application Priority Data
Jan. 19, 2017 (FR) .................................... 17 50423

(51) Int. Cl.
*B81C 1/00* (2006.01)
*G01N 30/66* (2006.01)
(Continued)

(52) U.S. Cl.
CPC ......... *G01N 30/66* (2013.01); *B81C 1/00103* (2013.01); *B81C 1/00246* (2013.01);
(Continued)

(58) Field of Classification Search
None
See application file for complete search history.

(56) References Cited

U.S. PATENT DOCUMENTS 9,187,320 B2 * 11/2015 Diem .................. H01L 21/3083
10,247,693 B2 * 4/2019 Che ..................... G01N 27/3272
(Continued)

FOREIGN PATENT DOCUMENTS

WO    WO 2015/161808 A1    10/2015

OTHER PUBLICATIONS

U.S. Appl. No. 15/388,673, filed Dec. 22, 2016, 2017/0184556 A1, Valeria Toffoli, et al.
(Continued)

*Primary Examiner* — Bradley Smith
(74) *Attorney, Agent, or Firm* — Oblon, McClelland, Maier & Neustadt, L.L.P.

(57) ABSTRACT

Method of fabricating a microelectromechanical structure et comprising two elements suspended from a support, a cavity made in the support, said cavity having two different depths, including:
 fabrication of a mask on an element comprising a substrate and a structured layer formed on the substrate, said structured layer comprising the two elements that will be suspended above the cavity, the mask being formed above the structured layer, said mask comprising openings with different sections, the openings being distributed in two zones, each zone comprising openings with the same section,
 anisotropic etching of the element so as to define the two depths under the two suspended elements in the substrate through the structured layer,
 isotropic etching of the element so as to make the cavity under the suspended elements.

13 Claims, 7 Drawing Sheets

(51) Int. Cl.
*G01N 25/48* (2006.01)
*G01N 33/00* (2006.01)

(52) U.S. Cl.
CPC ........ *B81C 1/00611* (2013.01); *G01N 25/482* (2013.01); *G01N 33/0031* (2013.01); *B81B 2203/0315* (2013.01); *B81B 2203/0384* (2013.01); *B81B 2203/0392* (2013.01); *B81C 2201/0132* (2013.01); *B81C 2201/0133* (2013.01)

(56) References Cited

U.S. PATENT DOCUMENTS

2012/0049313 A1 3/2012 Kwon et al.
2017/0363589 A1* 12/2017 Kumar ................... G01N 25/18

OTHER PUBLICATIONS

U.S. Appl. No. 15/454,249, filed Mar. 9, 2017, 2017/0261528 A1, Bruno Fain, et al.
U.S. Appl. No. 15/536,779, filed Jun. 16, 2017, 2017/0363493 A1, Bruno Fain, et al.
French Preliminary Search Report dated Sep. 15, 2017 in French Application 17 50423, filed on Jan. 19, 2017.
Phillip Zellner, et al. "A fabrication technology for three-dimensional micro total analysis systems", Journal of Micromechanics and Microengineering, Institute of Physics Publishing, vol. 20, No. 4, 2010, 8 pages.
G. De Graaf, et al. "Flow compensation in a MEMS dual-thermal conductivity detector for hydrogen sensing in natural gas", Transducers, 2015, 4 pages.

\* cited by examiner

METHOD OF FABRICATING A MEMS AND/OR NEMS STRUCTURE COMPRISING AT LEAST TWO ELEMENTS SUSPENDED FROM A SUPPORT AT DIFFERENT DISTANCES FROM SAID SUPPORT

TECHNICAL DOMAIN AND STATE OF PRIOR ART

This invention relates to a method of fabricating a microelectromechanical and/or nanoelectromechanical structure comprising at least two elements suspended from a support, the distance between each suspended element and the support being different from the distance between each other suspended element and the support.

One or several elements suspended from a support or substrate are frequently used in the domain of MEMS (Microelectromechanical systems) and/or NEMS (Nanoelectromechanical systems). The suspended elements can be used in devices operating on the principle of katharometric detection in which the conductivity is measured by measuring the temperature of a heating element. Such a heating element may for example be a wire suspended in a fluid cavity containing the gas or the gas mix to be analysed.

The element is suspended above a support forming a thermal reservoir at a given distance. However this distance, also called the gap, is an important characteristic in thermal conductivity measurements.

It may be useful to have a device comprising several elements suspended from a support, the distance between each suspended element and the support being different from the distance between each other suspended element and the support.

For example, the document "*Flow compensation in a MEMS dual-thermal conductivity detector for hydrogen sensing in natural gas*", G. de Graff et al. (*Transducers* 2015, Anchorage, USA) describes two membranes placed at different distances from a support, so that flow effects on measurements can be compensated. Each membrane is suspended above one chamber that is separated from the other chamber, the chambers having different depths.

The fabrication method mentioned in this document does not describe how the different depths are obtained.

PRESENTATION OF THE INVENTION

Consequently, one purpose of this invention is to disclose a method of fabricating a micromechanical and/or nanomechanical structure, for example MEMS and/or NEMS structure comprising several elements suspended from the same cavity inside which elements are suspended at different distances from the back of the cavity.

The purpose described above is achieved by a fabrication method according to which the starting point is a stack of at least one support and a structured layer containing the different suspended elements, a mask is placed above the structured layer, the mask comprising openings, the openings having at least two different sizes, each size being associated with at least one suspended element. The method also includes the application of anisotropic etching to etch the support to different depths dependent on the size of the openings and an isotropic etching to form at least one cavity under the suspended elements.

With the invention, it is then easy to simultaneously make different distances between the support and the suspended elements.

It is also possible to make a structure in which the elements are suspended in the same cavity and are located at different distances from the bottom of the cavity. To achieve this, the bottom of the cavity is structured with steps or with an approximately inclined plane.

In other words, the method uses the relation between the proportion of openings in the mask and the etching depth by distributing different sizes of openings above a structured layer containing the suspended elements, in the etching mask. It is then possible to etch under each suspended element to a given depth and individually fix a distance between a suspended element and the support.

In one example embodiment, the mask comprises n zones, each comprising openings of a given size different from the size of the openings in the other zones, each zone being located above a suspended element. The result obtained is thus a support comprising a bottom including different height steps depending on the size of the openings.

In another example embodiment, the suspended elements are arranged adjacent to each other along a given direction, and the size of the openings varies progressively and monotonously along one direction and the bottom approximately forms an inclined plane.

The method can be used to fabricate a structure comprising a large number of suspended elements without making the method more complicated.

The method according to the invention is particularly suitable for fabricating a device for analysis of a gas mix making use of katharometric detection and using several elements suspended at different distances from the bottom of a fluid cavity, to determine:
  in the case in which the gas mix comprises two species, the concentrations of the two species and the pressure of the gas mixture,
  in the case in which the gas mix comprises three species with known pressure, the concentrations of the three species of the gas mix.

The subject-matter of the invention is then a method of fabricating a microelectromechanical and/or nanoelectromechanical structure comprising n elements suspended from a support, n being an integer greater than or equal 2, a cavity made in the support, said cavity having m different depths along a direction orthogonal to a median plane of the structure, m being an integer greater than or equal 2, comprising:
  fabrication of a mask on a stack comprising a substrate and a structured layer formed on the substrate, said structured layer comprising the n elements that will be suspended above the cavity, the mask being formed above the structured layer, said mask comprising openings with different sections, the openings being distributed in at least m zones, each zone comprising openings with the same section,
  anisotropic etching of the substrate through the mask and the structured layer so as to define at least m depths in the substrate,
  isotropic etching of the substrate to form said cavity, the n elements then being suspended above the cavity.

BRIEF DESCRIPTION OF THE DRAWINGS

This invention will be better understood after reading the following description and the appended drawings on which.

DETAILED PRESENTATION OF PARTICULAR EMBODIMENTS

Figure 3:
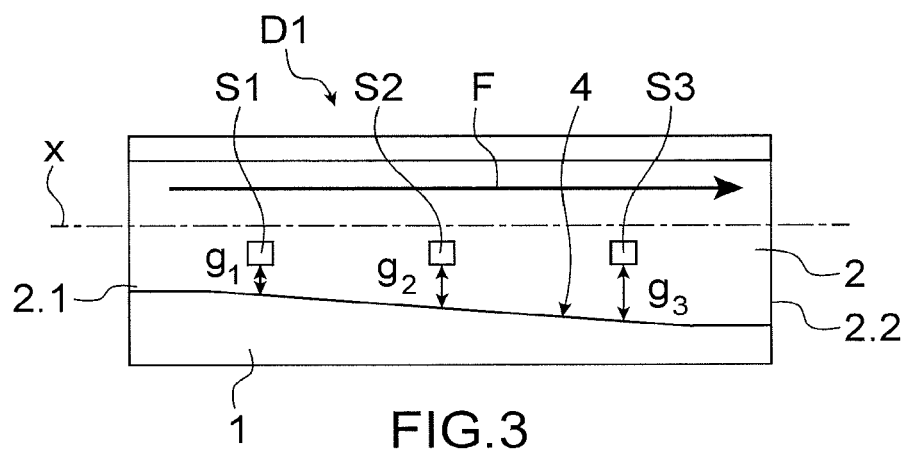
FIG. 3 is a diagrammatic longitudinal sectional view of an example embodiment of a structure that can be obtained by the method according to the invention and the mask 2B.
Figure 4:
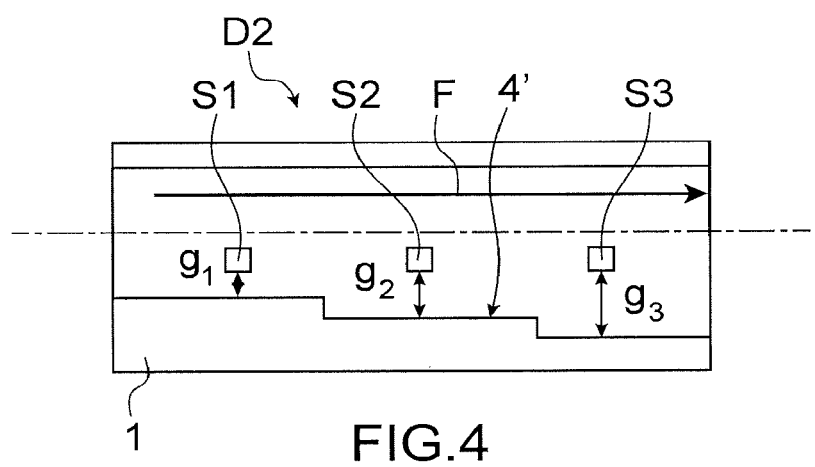
FIG. 4 is a diagrammatic longitudinal sectional view of another example embodiment of a structure that can be obtained by the method according to the invention and the mask 2A.

FIGS. 3 and 4 contain examples of structures that can be obtained using the method according to the invention.

On FIG. 3, the structure D1 comprises a support 1 and at least one channel 2 fabricated in this support 1. For example, the support may be a substrate, for example made of a semiconductor or glass. The channel comprises a bottom 4 and side walls.

The structure also comprises three measurement elements S1, S2, S3 located side by side along the direction F.

The median plane of the structure is the plane containing the suspended elements.

In the example shown, the measurement elements S1, S2, S3 are arranged to be parallel to each other and are suspended to be approximately perpendicular to the flow direction F.

The suspended elements may be in a very wide variety of shapes. FIGS. 5A to 5D show different example embodiments of a single measurement element seen from above and FIGS. 5A' and 5B' show sectional views along planes A-A' and B-B' in FIGS. 5A and 5B respectively, the sectional views in FIGS. 5C and 5D would be similar to FIG. 5B'.

Figures 5A, 5B:
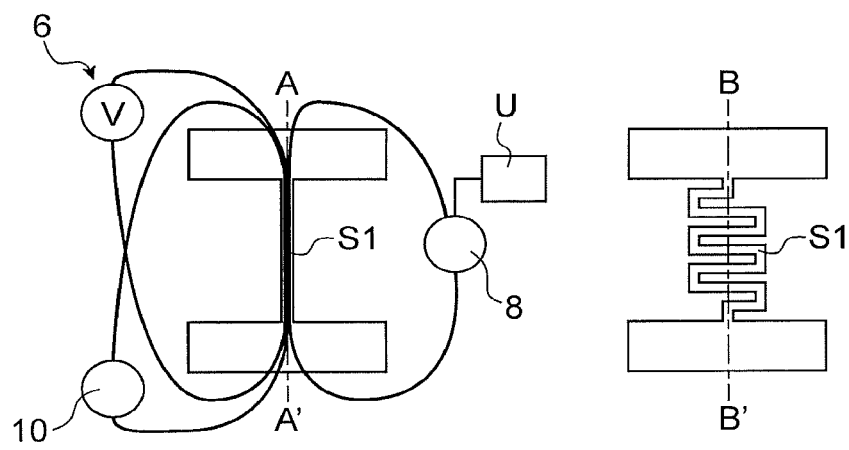
FIGS. 5A to 5D are top views of different examples of suspended elements that can be used by the method according to the invention, FIGS. 5A' and 5B' are cross-sectional views along planes A-A' and B-B' on FIGS. 5A and 5B respectively.
Figures 5C, 5D:
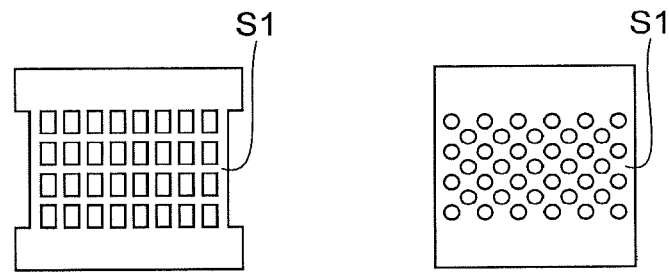
Figures 5A, 5B:
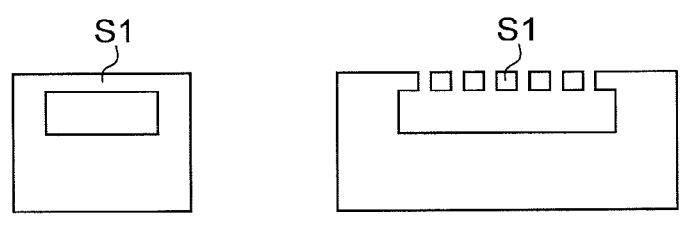

On FIG. 5A, the measurement element is a straight wire, on FIG. 5B it is a zigzag shaped wire, and on FIGS. 5C and 5D, measurement elements are perforated suspended membranes. As a variant, the membranes could be solid. Preferably, all measurement elements of a sensor have an identical or similar structure.

It could be envisaged to functionalise the surface of measurement elements. In this case, the properties of measurement elements are modified by the chemical species present in the gas phase, for example the mass.

Measurement element S1 is at a distance g1 from the bottom of the channel, measurement element S2 is at a distance g2 from the bottom of the channel and measurement element S3 is at a distance g3 from the bottom of the channel.

The distances g1, g2 and g3 are different. In the example shown, g1 is less than g2, that is itself less than g3.

In the example shown, the bottom 4 of the channel is inclined downwards in the F direction and is contained in a plane.

On FIG. 4, the structure D2 comprises a stepped bottom 4' and is therefore contained in several parallel planes.

In the described examples, the distance between the suspended element and the bottom of the channel varies monotonously. But with the method according to the invention, it would be possible to envisage g1 and g3 being greater than and g2 and g3 being greater than g1.

Figure 1A:
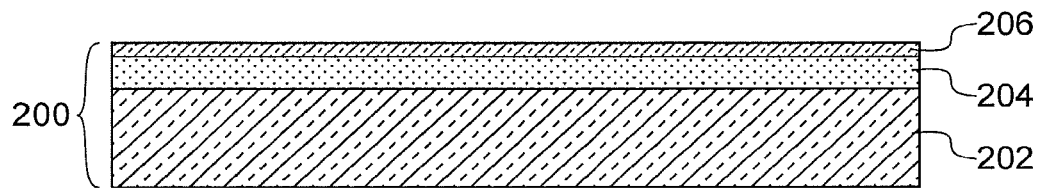
FIGS. 1A to 1R are diagrammatic views of elements obtained during steps in an example fabrication method according to the invention.

One example of the method of fabricating an analysis device similar to that in FIG. 4 according to the invention comprising two measurement elements according to the invention will now be described with reference to FIGS. 1A to 1R.

For example, a Silicon On Insulator (SOI) substrate 200 can be used. The substrate is shown on FIG. 1A. The substrate 200 comprises a silicon support substrate 202, a silicon oxide layer 204 and a monocrystalline silicon layer 206 on the oxide layer 204. As a variant, the substrate may be an oxidised silicon (Si) substrate on which a layer of amorphous or polycrystalline Si is formed.

Figure 1B:
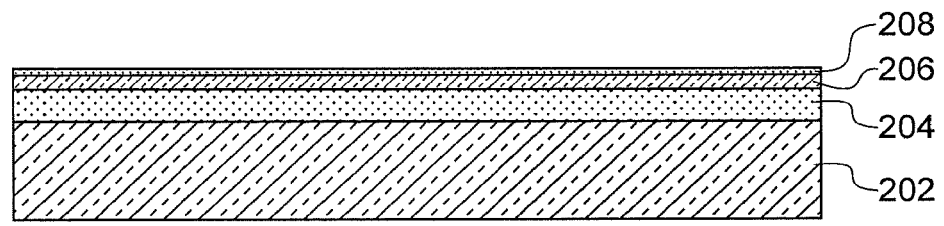

During the next step, an oxide layer 208 is formed on the layer 206, and a boron ion implantation is then made. The element thus obtained is shown on FIG. 1B.

Figure 1C:
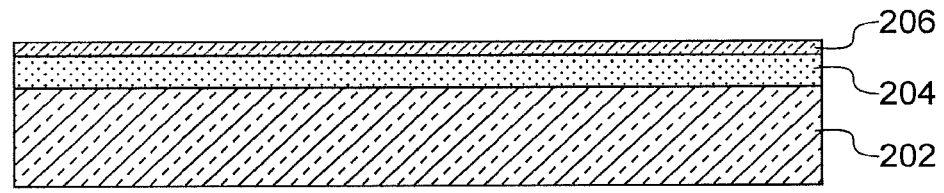

During the next step, the oxide layer is removed, for example by chemical etching based on hydrofluoric acid (HF). The element thus obtained is shown on FIG. 1C.

During the next step, the silicon layer 206 is structured for example by photolithography and etching so as to form the measurement elements.

Figure 1D:
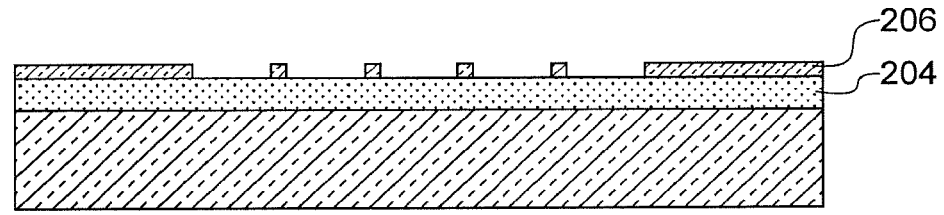

The element thus obtained is shown on FIG. 1D.

During the next step, a protective layer 210 is formed on the sensitive elements, for example it may be an oxide layer for example 500 nm thick. For example, the layer 210 may be deposited by a chemical vapour deposition technique. The layer 210 is then planarised.

Figure 1E:
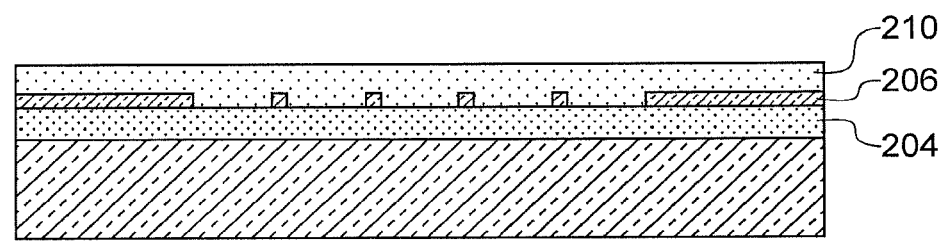

The element thus obtained is shown on FIG. 1E.

During the next step, the layer 210 is structured to form accesses 212 to the layer 206 outside the part containing the measurement elements. This structure is made by photolithography and etching.

Figure 1F:
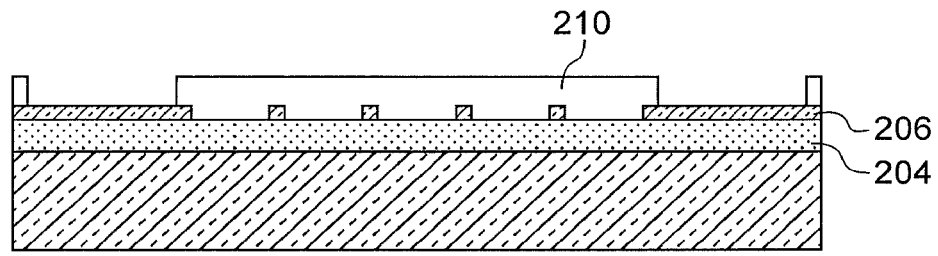

The element thus obtained is shown on FIG. 1F.

In the next step, contact pads 213 are made at the accesses 212. A metallic layer 214, for example made of AlSi, is formed on the layer 210, for example by deposition, and is then structured for example by etching.

Figure 1G:
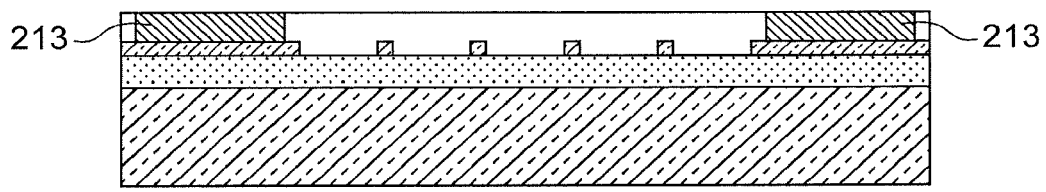

The element thus obtained is shown on FIG. 1G.

Another oxide layer 216 is formed on the layer 210 and on the contact pads 213 during a next step, for example by deposition. For example, it may be 1 µm thick. A layer 218 of amorphous Si is then formed on the layer 216, for example 100 nm thick. The layer 218 can be formed from any material that is resistant to HF and that can be etched by photo-lithography, for example boron nitride.

Figure 1H:
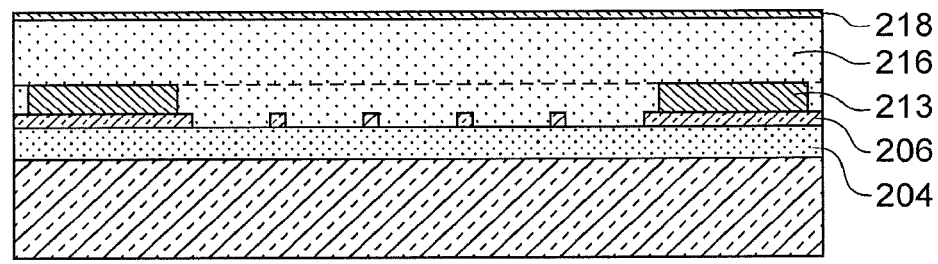

The element thus obtained is shown on FIG. 1H.

During the next step, the layers 216 and 218 are structured to expose the active part of the sensor, this structuring being done for example by photolithography and etching.

Figure 1I:
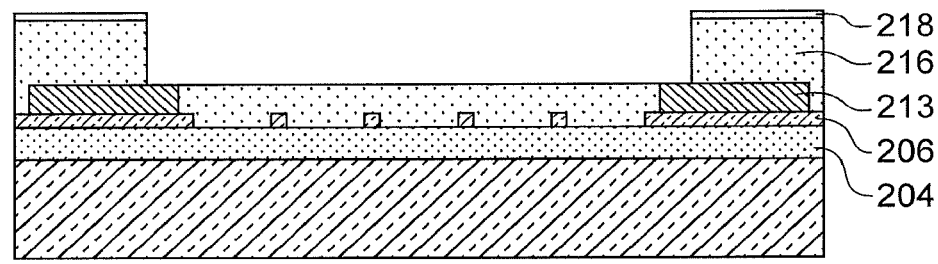

The element thus obtained is shown on FIG. 1I.

The elements obtained with the following steps are represented in two section planes at each measurement element.

During a next step, an oxide layer 220 is deposited. A resin layer 221 is then deposited and will form a mask.

During a next step, the layer 221 is structured by photolithography so as to form openings in the layer 221.

Figure 1J:
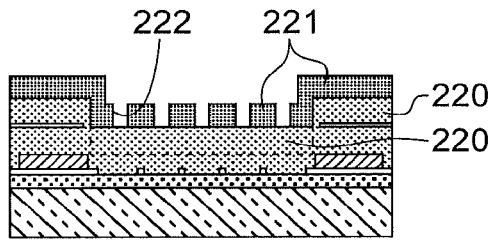
Figure 1J:
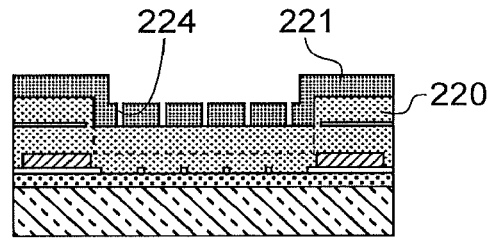

The photolithography step is such that first openings 222 with a first section are made in a zone A1 of the layer 221 at the first measurement element S1 (FIG. 1J) and second openings 224 with a second section are made in a zone of the layer 220 at the first measurement element S2 (FIG. 1J'). The first section and the second section are different. In the example shown, the first section is larger than the second section.

Figure 2A:
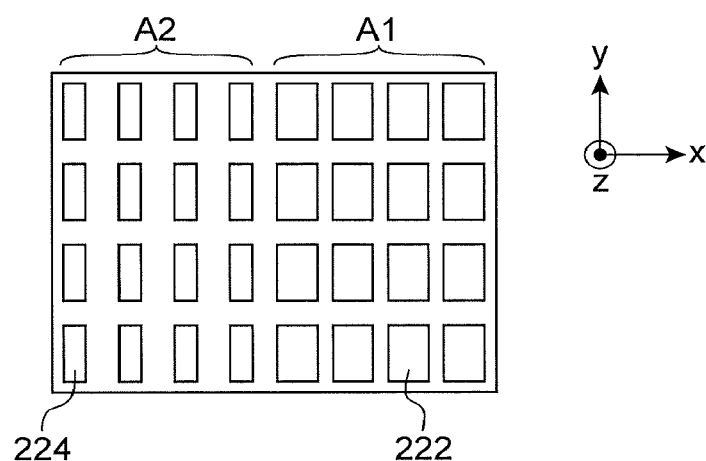
FIGS. 2A and 2B are top views of the elements of FIGS. 1J and 1J'.

FIG. 2A shows a diagrammatic top view of the element in FIGS. 1J and 1J'. The two zones A1, A2 of the mask 221 with openings 222 and 224 with different sections can be seen. This mask 221 can be used to make a structure comprising two steps as shown on FIG. 4.

The mask 221 comprises columns of openings adjacent to each other. In the example shown, several columns have openings with the same section. The columns extend over the entire width of the suspended elements in the Y direction.

The section of the openings in the mask determines the etching depth as will be explained below. By making two zones each with openings of a given section, it is possible to make etchings with two different depths.

Another function of the mask formed in the oxide layer is to make it possible to structure the different layers around the measurement elements.

In order to fabricate structure D2, the mask comprises three zones with openings with different sections.

Figure 2B:
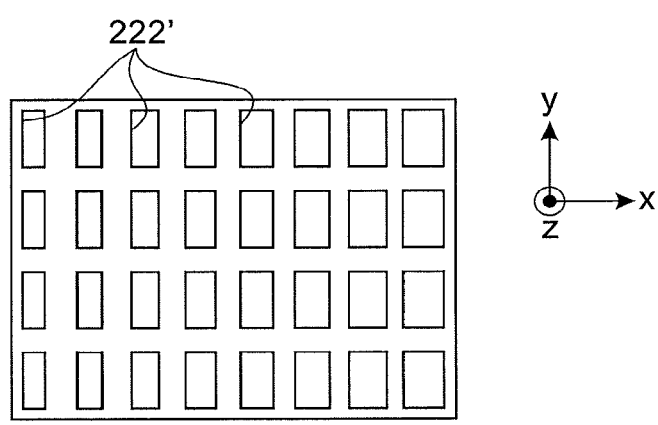

FIG. 2B shows another example embodiment of a mask in which the section of the openings varies progressively and monotonously along the X direction, to make an approximately plane inclined bottom as shown on FIG. 3. In the example shown, the sections of the openings 222' vary from one column to the other and increases from left to right in the view shown on FIG. 2B.

The variation of the section of the openings is very progressive from one column of openings to the next and the openings are very close to each other to assure quasi-continuity of the etching depth and to limit the occurrence of a step.

In another variant, the two masks in FIGS. 2A and 2B could be combined to make a cavity in which the depth could comprise level parts and inclined parts.

In the examples in FIGS. 2A and 2B, the openings are rectangular in shape but this is not limitative, they could be square or round, etc.

During the next step, etching is done until reaching the substrate 200, for example by anistropic etching. Openings reaching the substrate 200 with the first section are thus formed in the first zone and openings reaching the substrate 202 with the second section are thus formed in the second zone.

Figure 1K:
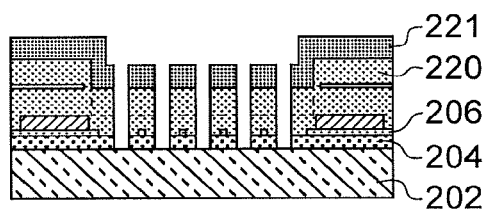
Figure 1K:
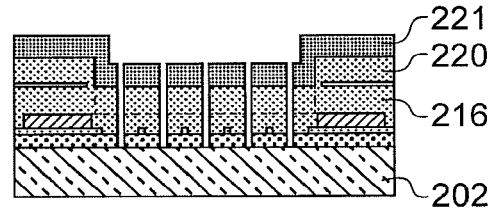

The element thus obtained is shown on FIGS. 1K, 1K'.

During the next step, the substrate is etched, by anisotropic etching, for example by Deep Reactive Ion Etching (DRIE). Since the section of the openings in the first zone A1 are larger than in the second zone A2, etching in substrate 202 is deeper under the first zone A1 than under the second zone A2. The substrate then comprises a plurality of cavities with a depth that depends on the section of the opening through which it was etched.

Figure 1L:
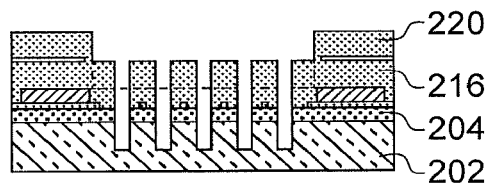
Figure 1L:
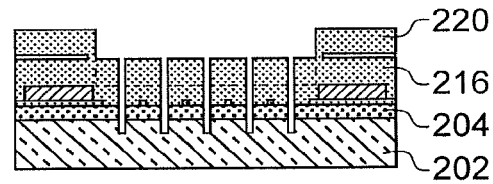

The element thus obtained is shown on FIGS. 1L and 1L'.

In the next step, the substrate 202 is structured to combine the openings in the first zone and the openings in the second zone. This structure may for example be made by isotropic etching. This etching etches the side walls of the cavities that are then combined into a single cavity. Another purpose of isotropic etching is to etch the substrate towards the outside under the contact pads, the thickness of the material between the cavities is then such that during isotropic etching, this entire thickness is etched before excessive etching occurs at the contact pads. Separations between openings in the mask are then chosen accordingly. The isotropic etching can be a reaction ion etching. The isotropic etching can be made by using gas, for example $SF_6$.

In this example, taking account of the quantity of oxide encapsulating the Si nanostructures and the ratio of the selectivity of isotropic Si etching to $SiO_2$ that is equal to about 1000, the distance between openings can be as much as 50 μm.

Reaction ion etching can be isotropic etching or anisotropic etching depending on the operating conditions, for example on the polarization voltage applied to the substrate.

Figure 1M:
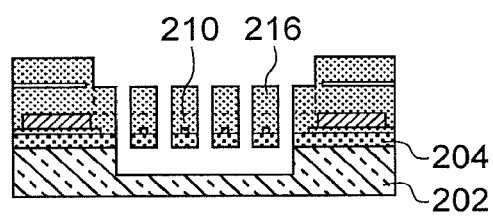
Figure 1M:
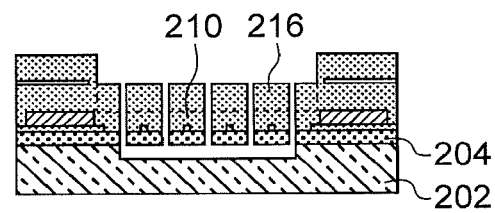

The element thus obtained is shown on FIGS. 1M, 1M and corresponds to the structure according to the invention.

During a next step, the oxide in layers 204, 210 and 216 around the suspended elements is removed for example by hydrofluoric acid.

Figure 1N:
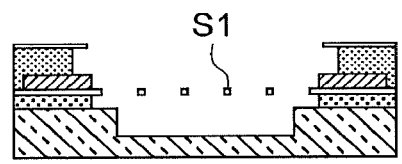
Figure 1N:
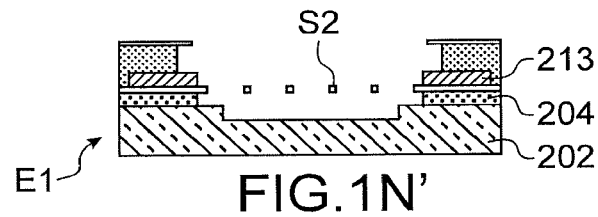

The element E1 thus obtained is shown on FIGS. 1N and 1N'.

Depending on the use made of the structure in FIGS. 1N and 1N', it could be envisaged to add a cap to it to form a closed cavity and/or to protect the suspended elements.

We will now describe an example to make such a cap and its assembly to the structure in FIGS. 1N and 1N'.

A cap is fabricated separately, for example from a substrate 300 made of silicon, another semiconducting material or even a substrate could be suitable.

Figure 1O:
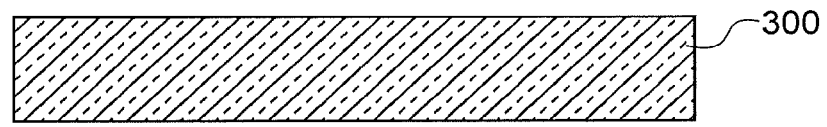

The substrate 300 is shown on FIG. 1O.

An opening or a recess 302 is shown on the front face of the substrate, for example 100 μm deep, for example by photolithography and etching.

Figure 1P:
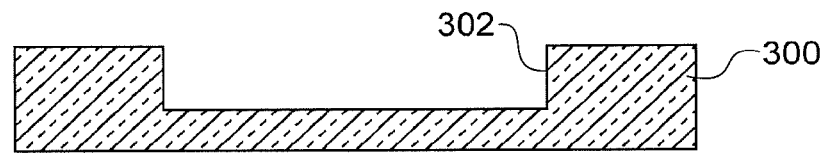

The element thus obtained is shown on FIG. 1P.

During a next step, a sealing bead 304 is formed on the front face so as to surround the recess. For example, the bead may be made of a polymer material and it may be deposited.

Figure 1Q:

The element E2 thus obtained is shown on FIG. 1Q.

During a next step, the element E1 is bonded onto the element E2 such that the recess is facing the measurement elements. For example, bonding may be done by thermocompression.

Other types of mechanical bonding with beads that enable Au/Au thermocompression bonding, Au/Si eutectic bonding could be envisaged.

Figure 1R:
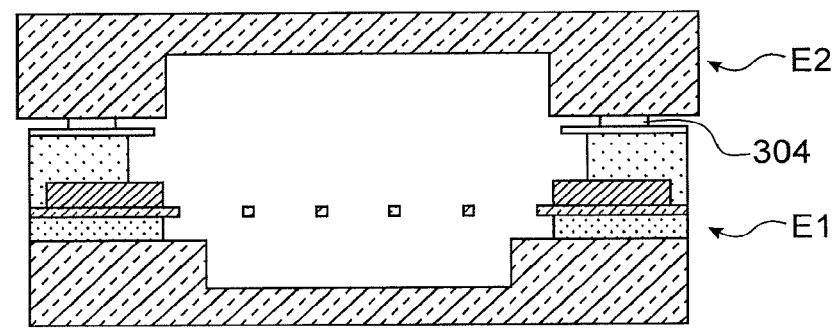

The element thus obtained is shown on FIG. 1R and forms the analysis device. The contact pads are configured to be connected to an electronic circuit that comprises means for polarising the measurement elements, for measuring the electrical resistances of measurement elements and for processing measurements to determine the concentration of gas species and possible the mix pressure.

It will be understood that the method according to the invention is applicable to manufacturing of a structure with n suspended elements, each suspended element being at a different distance from the support, where n is an integer greater than or equal to 2. The method can advantageously be used to fabricate a large number of suspended elements simultaneously without making the process more complex.

As a variant, the sections of openings in the mask could be distributed such that the depth of the bottom increases monotonously. For example, four zones of openings could be provided, a first zone with openings with section s1, a second zone with openings with section s2, a third zone with openings with section s3 and a fourth zone with openings with section s4. The zones would be arranged adjacent to each other along the X direction from the first zone to the fourth zone, section s1 being less than s2, s2 is less than s3 and s3 is greater than s4.

Similarly in the case of openings with a section that varies progressively, it would be possible that the progressive variation is not monotonous. The bottom of the cavity would then include slopes with opposite orientations.

As another variant, a variation of the depth in the Y direction, possibly but not necessarily associated with a variation of the depth in the X direction, is within the scope of this invention.

In the example method described above, all the suspended elements are suspended in the same cavity, but it would be possible to envisage them being suspended in distinct cavities and making cavities with different depths simultaneously, each cavity possibly having several depths.

It will also be understood that although production of different depths under the suspended elements has been described in detail, the isotropic and anisotropic etching steps also act on zones between the suspended elements.

The distance between columns of openings is fixed by the layout and shape of the suspended elements.

In the case of suspended elements formed from membranes comprising holes, the openings in the masks are aligned with spaces between membranes and with holes in the membranes.

It will also be understood that several successive suspended elements could be at the same distance from the bottom of the cavity, for example the bottom of the cavity could comprise level parts extending under several suspended elements.

The fabrication method according to the invention is particularly suitable for fabrication of a device for analysis of a gas mix making use of katharometric detection comprising several elements suspended at different distances from a support forming a thermal reservoir. The cavity forms a channel through which the gas mix to be analysed is supplied.

The device also comprises means 6 of polarising the suspended elements, means 10 of heating the suspended elements and means 8 of measuring the electrical resistance of the suspended elements (FIG. 5A).

The electrical resistances of the suspended elements are measured.

Knowing the function relating the thermal conductivity to the measured electrical resistance for each suspended element, it is possible to determine the composition of the gas mix.

By using elements suspended at different heights and taking account of the free path of the gas mix that depends on the distance between the suspended elements and the support, it is possible to determine the composition of a mix of two species and its pressure and to determine the composition of a mix of three species, knowing the pressure of the gas mix.

The invention claimed is:

1. A method of fabricating a microelectromechanical and/or nanoelectromechanical structure comprising n elements suspended from a support, n being an integer greater than or equal 2, a cavity made in the support, said cavity having m different depths along a direction orthogonal to a median plane of the structure, m being an integer greater than or equal 2, comprising:
   fabrication of a mask on a stack comprising a substrate and a structured layer formed on the substrate, said structured layer comprising the n elements that will be suspended above the cavity, the mask being formed above the structured layer, said mask comprising openings with different sections, the openings being distributed in at least m zones, each zone comprising openings with the same section;
   anisotropic etching of the substrate through the mask and the structured layer to make the at least m zones at different depths so as to define at least m depths in the substrate; and
   isotropic etching of the substrate to form said cavity connecting the at least m etched zones, the n elements then being suspended above the cavity,
   wherein the isotropic etching is a reactive ion etching, and wherein the anisotropic etching is a deep reactive ion etching.

2. The fabrication method according to claim 1, wherein the cavity has a first dimension and a second dimension along orthogonal directions and contained in a median plane of the structure, and
   wherein the openings in the etching mask are distributed approximately in rows and columns, the rows being aligned along the direction of the first dimension of the cavity and the columns being aligned along the direction of the second dimension.

3. The fabrication method according to claim 2, wherein each zone comprises several successive columns, the sections of the openings being identical for each column in the same zone and different for columns in different zones, so as to form a cavity comprising a bottom with steps of different depths, each step corresponding to a zone.

4. The fabrication method according to claim 2, wherein each zone comprises a column, the section of the openings in each column varying monotonously at least along the direction of the first dimension so as to form a cavity with a bottom approximately forming an inclined plane.

5. The fabrication method according to claim 1, wherein each zone is formed at least vertically in line with one element of the structured layer and the openings in each zone are formed at least vertically in line with spaces between two elements of the structured layer.

6. The fabrication method according to claim 5, wherein the elements that will be suspended are membranes provided with holes, openings in each zone of the etching mask also being formed vertically in line with holes in the membranes.

7. The fabrication method according to claim 1, wherein the stack comprises a sacrificial layer between the structured layer and the substrate, the method also comprises a step in which the sacrificial layer is removed to release suspended elements from the sacrificial layer.

8. The fabrication method according to claim 1, wherein the structure layer is made of Si or SiN+Pt.

9. The fabrication method according to claim 8, wherein the stack is made from an SOI substrate and in which the structured layer is obtained by structuring of the monocrystalline silicon layer.

10. The fabrication method according to claim 1, further comprising bonding a cap after the suspended elements have been released, above the cavity and facing the suspended elements.

11. The fabrication method according to claim 1, wherein n is equal to m and each suspended element is suspended above the cavity at a different distance from the bottom of the cavity.

12. The fabrication method of fabricating a device for analysis of a gas mix making use of the method according to claim 1 and further comprising:
   fabrication of electrical connections at the suspended elements;
   fabrication of an heating for heating the suspended elements; and
   connection of suspended elements to a polarization circuitry and to a sensor for measuring the electrical resistance of the suspended elements.

13. The fabrication method according to claim 7, wherein the stack comprises a sacrificial layer between the structured layer and the substrate, the method also comprises a step in which the sacrificial layer is removed to release suspended elements from the sacrificial layer, by means of hydrofluoric acid.

* * * * *